United States Patent
Chaudhuri et al.

(10) Patent No.: US 11,759,434 B2
(45) Date of Patent: Sep. 19, 2023

(54) METHODS AND COMPOSITIONS FOR TREATING MELANOMA AND NON-MELANOMA SKIN CANCERS

(71) Applicant: Sytheon Limited, Parsippany, NJ (US)

(72) Inventors: Ratan K Chaudhuri, Lincoln Park, NJ (US); Sanjay Premi, Wesley Chapel, FL (US)

(73) Assignee: Sytheon Limited, Parsippany, NJ (US)

( * ) Notice: Subject to any disclaimer, the term of this patent is extended or adjusted under 35 U.S.C. 154(b) by 0 days.

(21) Appl. No.: 18/101,082

(22) Filed: Jan. 24, 2023

(65) Prior Publication Data
US 2023/0241007 A1    Aug. 3, 2023

Related U.S. Application Data

(60) Provisional application No. 63/306,253, filed on Feb. 3, 2022, provisional application No. 63/306,246, filed on Feb. 3, 2022.

(51) Int. Cl.
| | |
|---|---|
| *A61K 31/12* | (2006.01) |
| *A61K 31/519* | (2006.01) |
| *A61P 17/00* | (2006.01) |
| *A61P 35/00* | (2006.01) |

(52) U.S. Cl.
CPC ............ *A61K 31/12* (2013.01); *A61K 31/519* (2013.01); *A61P 17/00* (2018.01); *A61P 35/00* (2018.01)

(58) Field of Classification Search
CPC ................................ A61P 17/00; A61P 35/00
See application file for complete search history.

(56) References Cited

U.S. PATENT DOCUMENTS

| 10,568,819 B2 | 2/2020 | Chaudhuri |
| 10,828,241 B2 | 11/2020 | Chaudhuri |

OTHER PUBLICATIONS

Zink et al., Structural variations of piritrexim, a lipophilic inhibitor of human dihydrofolate reductase: synthesis, antitumor activity and molecular modeling investigations, European J. of Med. Chem., 39, 1079-1088 (2004) (Year: 2004).*

Chaudhuri RK et. al., "Acetyl Zingerone: An Efficacious Multifunctional Ingredient for Continued Protection Against Ongoing DNA Damage in Melanocytes After Sun Exposure," Int'l J. Cosmetic Sci., 2019, 1-10 DOI:10.1111/ics.12582.

Chen, L et.al., "AMPK Activation by GSK621 Inhibits Human Melanoma Cells in vitro and in vivo," Biochemical and Biophysical Research Communications, 480 (2016), 515-521.

* cited by examiner

*Primary Examiner* — Erich A Leeser
(74) *Attorney, Agent, or Firm* — Hoffmann & Baron, LLP; Edward K Welch, II

(57) ABSTRACT

Compositions comprising select aryl alkanones and the use thereof in the treatment of melanoma and non-melanoma skin cancer.

21 Claims, 1 Drawing Sheet

METHODS AND COMPOSITIONS FOR TREATING MELANOMA AND NON-MELANOMA SKIN CANCERS

RELATED APPLICATIONS

The present application claims the benefit of U.S. Provisional Application Ser. Nos. 63/306,246 and 63/306,253 filed 3 Feb. 2022 entitled "Methods and Compositions for Treating and Preventing Cancer," the contents of both of which are hereby incorporated herein by reference in their entirety.

TECHNICAL FIELD

The present teachings relate to select aryl alkanone compounds and compositions for use in the treatment of melanoma and non-melanoma skin cancers as well as the use thereof in the treatment of melanoma and non-melanoma skin cancers.

BACKGROUND

According to the World Health Organization (WHO) cancer is a leading cause of death worldwide. The disease accounted for about 19.3 million new cases and 10 million deaths worldwide in 2020. The main types of cancer leading to overall cancer mortality each year are: lung (1.8 million deaths), colorectal (916,000 deaths), liver (830,000 deaths), stomach (769,000 deaths), and female breast cancer (685,000 deaths). The global cancer burden is projected to continue to rise to 28.4 million cases by the year 2040.

During a cell's normal lifecycle, it encounters numerous challenges where it must decide whether to proliferate, differentiate or die. A defect in any of these processes may result in cancer, or the uncontrolled growth of the cell. Cancer, in general, has traditionally been treated with one or more, preferably a combination of, three types of therapies: surgery, radiation, and chemotherapy. The adverse effects of systemic chemotherapy are feared the most by patients; these can include nausea, vomiting, and a wide range of complications that impact on the patient's quality of life. Pain is a prevalent symptom in cancer patients, affecting up to 50% of patients undergoing active cancer treatment and up to 90% of those with advanced disease. In addition to the physical and emotional suffering due to the diagnosis of cancer, patients are subjected to additional discomfort, and symptoms associated with both the disease and its treatment.

Though not a leading type of cancer skin cancers are among the deadliest with melanoma being the deadliest form of skin cancer. In 2020 on a world-wide basis, non-melanoma skin cancer was responsible for over 1.2 million new cases (excluding basal cell carcinoma) and 64,000 deaths with melanoma skin cancer adding a further 325,000 new cases and 57,000 deaths. Melanoma has a high propensity for hematogenous and lymphatic dissemination to regional and distant sites in the body and is poorly responsive to most systemic therapies. The 5-year survival rate for metastatic melanoma is dismal, ranging from 5% to 10% with a median survival of less than 8 months with treatment.

It is well established that many molecules, particularly cellular DNA, in the skin absorb ultraviolet (UV) radiation upon exposure. In particular, cellular DNA strongly absorbs shorter wavelength solar UV radiation resulting in various types of DNA damage as well as the production of various DNA photoproducts including, predominantly, cyclobutane pyrimidine dimers (CPDs), Although these lesions are efficiently repaired by one's natural processes in the skin, CPD also formation results in various acute effects (erythema, inflammatory responses), transient effects (suppression of immune function), and chronic effects (mutation induction and skin cancer). Statistics are now indicating that the rate of increase in both melanoma and non-melanoma skin cancers is beginning to slow down due to the extensive efforts to raise awareness and teach preventative measures such as sun avoidance, application of full-spectrum sunscreens and use of antioxidant creams. Despite these advances, the absolute numbers continue to climb due to the shortcomings of the current preventative measures. For example, neither sunscreens nor topical antioxidants have been shown to effectively block the effects of UV radiation. In part, the level of antioxidants contained in the majority of skin creams is too low or ineffective to have a major impact on free radical damage. Similarly, sunscreens absorb only a portion of UV radiation and many fail to be photostable following a few minutes of sun exposure [H Gonzalez, N Tarras-Wahlberg, B Stromdahl, A Juzeniene, J Moan, O Larko, A Rosen, A M Wennberg, Photostability of commercial sunscreens upon sun exposure and irradiation by ultraviolet lamps, BMC Dermaotology, 7:1 (2007) www.biomedicalcentral.com/1471-5945/7/1]. Furthermore, observational studies have repeatedly found sunscreen use to be associated with higher risk of cutaneous melanoma and basal cell skin cancer. This correlation is hypothesized to exist because sunscreens delay the appearance of sunburn, encouraging prolonged sun exposure and thereby increasing skin cancer risk [Vasmeen Kabir, Rachel Seidel, Braden Mcknight, Ronald Moy, DNA Repair Enzymes: An Important Role in Skin Cancer Prevention and Reversal of Photodamage—A Review of the Literature, J Drugs Dermatol. 14(3):297-301, 2015].

Melanoma is a malignant tumor of melanocytes, cells that are derived from the neural crest. Although most melanomas arise in the skin, they may also arise from mucosal surfaces or develop at other sites to which neural crest cells migrate. More than half of primary melanomas occur in areas of the skin often exposed to the sun. Early signs suggesting malignant change include darker or variable discoloration of the skin, itching, an increase in size of colored domains, or the development of small new patches of color (satellites) around a larger lesion. Ulceration and/or bleeding are later signs. Melanoma most often appears on the trunk, head, or neck of affected men. In women, this type of cancer most often develops on the lower legs. In both men and women, melanoma can occur on skin that hasn't been exposed to the sun. Melanoma can affect people of any skin tone. In people with darker skin tones, melanoma tends to occur on the palms or soles, or under the fingernails or toenails. Although early-stage disease is curable by surgery, the prognosis associated with metastasis to distant sites is poor; and median survival is only 4 to 6 months. With no sensitive tools available to monitor therapy and follow-up, these statistics reflect the unpredictable pattern of recurrence of melanoma, as well as its resistance to treatment by radiation and chemotherapy.

Melanoma, when detected at later stages is arguably one of the most lethal cancers and the cause of more years of lost life than any other cancer among young adults. There is no standard therapy for advanced-stage melanoma and the median survival time for patients with metastatic melanoma is <1 yr. With such a dismal prognosis and lack of successful therapies and the continued growth in the numbers of individuals being diagnosed with melanoma, there is a huge unmet need to identify means to effectively treat melanoma and, most importantly, to retard and/or mitigate its manifestation and proliferation.

Further exacerbating the issue of skin cancer and melanoma is the well-known fact that chronic exposure to UV and ionizing radiation leads to DNA damage. This process underlies photoaging, a term that broadly encompasses changes in the skin associated with life-long exposure to the sun: wrinkling, skin laxity, erythema, and hyperpigmentation. More important from a clinical perspective is the well-documented role of DNA damage as the provoking event in mutagenesis and tumor development. DNA damage induced by ultraviolet radiation (UVR) is considered to play a direct part in the initiation of skin cancers.

DNA damage arising from UV exposure is arguably one of the most, if not the most, relevant type of photodamage initiated by sun exposure. As noted above, research has identified dipyrimidine lesions, most notably cyclobutane pyrimidine dimers (CPDs) and 6-4 pyrimidine-pyrimidone photoproducts as the predominant products of such DNA photodamage: GPD constituting ≈80% of the total lesions. More recent studies have also identified CPDs as the main class of DNA lesions responsible for induction of melanoma and non-melanoma skin cancers [Douki, T, Sunlight-Induced DNA Damage: Molecular Mechanisms and Photoprotection Strategies," Skin Stress Response Pathways (Wondrak, G. T. ed.), pp, 49-77, 2016— DOI: 10.1007/978-3-319-43157-4_3; G P Pfeifer and A Besaratinia, UV wavelength-dependent DNA damage and human non-melanoma and melanoma skin cancer, Photochem Photobiol Sci, 11:90-97, 2012].

Previously, Brash et al had shown that Chemiexcitation of melanin derivatives induces DNA photoproducts long after UV exposure [S Premi, S Wallisch, C M Mano, A B Weiner, A Bacchiocchi, K Wakamatsu, E J H Bechara, R Halaban, T Douki, D E Brash, Chemiexcitation of melanin derivatives induces DNA photoproducts long after UV exposure, Science, 347(6224):842-847, 2015]. These authors have further demonstrated that the presence of melanin, activation of iNOS and NOX, and the triplet state were required for dark CPD formation.

More recently, Chaudhuri et al. affirmed the continued production of CPDs long after UV exposure ended (these CPDs often referred to as dark-CPDs or dCPDs) and found that acetyl zingerone was efficacious in inhibiting dCPD formation and proposed its use as an additive to sunscreen and daily skin care formulations for that specific purpose. [Chaudhuri, R K et. al., Acetyl Zingerone: An Efficacious Multifunctional Ingredient for Continued Protection Against Ongoing DNA Damage in Melanocytes Afterr Sun Exposure Ends," International Journal of Cosmetic Science, 2019, 1-10—DOI:10.1111/ics.12582].

Despite these advances in preventative measures and sun protective products, melanoma and non-melanoma skin cancers continue to proliferate and survival rates continue to be dismal, especially as compared to advancements being made against other cancers. Indeed, melanoma continues to be extremely lethal.

In following there continues to be an urgent and huge unmet need to develop effective methods and compositions that can treat skin cancers as well as methods and compositions that can mitigate and/or delay its onset and proliferation.

SUMMARY OF THE INVENTION

Surprisingly, it has now been found that certain aryl alkanones according to Structure 1

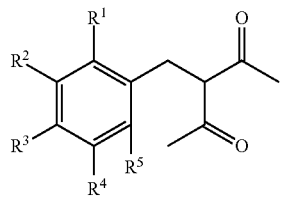

wherein $R_1$, $R_2$, $R_3$, $R_4$ and $R_5$, which may be the same or different, are each independently H, OH, alkyl or alkoxy, provided that at least one of $R_1$, $R_2$, $R_4$ and $R_5$ is not H, preferably at least one of $R_1$, $R_2$, $R_3$, $R_4$ and $R_5$ is OH or $OCH_3$, and wherein the alkyl or alkoxy groups, if present, are linear or branched and have from 1 to 8 carbon atoms, preferably from 1 to 6 carbon atoms, most preferably from 1 to 4 carbon atoms, are very effective in up-regulating genes that are adversely affected by, particularly down regulated by, non-melanoma skin cancers and/or melanoma and in down-regulating genes that are otherwise up-regulated by non-melanoma skin cancers and melanoma as well as in the treatment of such cancers. In particular, these compounds have been found to be effective for treating melanoma and non-melanoma skin cancers, especially in mitigating, interfering with and/or reversing the proliferation, including metastization, of non-melanoma and melanoma skin cancers, particularly in humans. Preferably the compounds of Structure 1 are those wherein $R_1$, $R_2$, $R_3$, $R_4$ and $R_5$ are H, OH or alkoxy. More preferably, the compounds of Structure 1 are those wherein $R_1$ and $R_2$ are H and $R_3$, $R_4$ and $R_5$, which may be the same or different, are each independently H, OH, or $C_1$ to $C_4$ alkoxy, provided that at least one of $R_3$, $R_4$ and $R_5$ is not H.

In following, in accordance with the present teaching there are provided topical, oral, intravenous, intraperitoneal, and/or subcutaneous administrable compositions comprising at least one compound according to Structure 1 Typically, and preferably, these compositions also include a suitable carrier, particularly, depending upon the mode of administration, a pharmaceutically acceptable carrier. Preferably, the amount of the compound(s) according to Structure 1 in such compositions is from 0.05 to 25 percent, preferably from 0.1 to 20 percent, more preferably from 0.5 to 15 percent by weight based on the total weight of the composition. These compositions may further contain other ingredients commonly co-administered with anti-cancer therapeutic, especially immuno- and chemo-therapeutic, active agents and the like, in conventional amounts.

In accordance with another aspect of the present teaching there are provided topical, oral, intravenous, intraperitoneal and/or subcutaneous administrable compositions comprising at least one compound according to Structure 1 in combination with at least one other anti-cancer therapeutic, especially immuno- and/or chemo-therapeutic, active agents for the treatment of melanoma and/or non-melanoma skin cancer. Typically, and preferably, these compositions also include a suitable carrier, particularly, depending upon the mode of administration, a pharmaceutically acceptable carrier. The other anti-cancer active agents are those known or believed or suspected to be suitable for use in the treatment of non-melanoma and/or melanoma skin cancers. Exemplary anti-cancer active agents include, but are not limited to, dacarbazine; AMPK activator; immune checkpoint inhibitors (ICI); BRAE and MEK inhibitors, including dabrafenib (Tafinlar), trametinib (Mekinist), vemurafenib (Zelboraf), cobimetinib (Cotellic), encorafenib (Braftovi) and binimetinib (Mektovi); PD-1 inhibitors, including pembrolizumab (Keytruda) and nivolumab (Opdivo); CTLA-4 inhibitors, including ipilimumab (Yervoy), and the like, as well as combinations of any two or more of the foregoing. Indeed, suitable combinations of such anti-cancer active agents are already well known and/or in development. Preferably, the amount of the compound(s) according to Structure 1 in such compositions is from 0.05 to 25 percent, preferably from 0.1 to 20 percent, more preferably from 0.5 to 5 percent by weight based on the total weight of the composition. The other anti-cancer agents are present in their conventional therapeutically effective amounts; however, as there appears to be a level of synergy that arises with the combination of compounds according to Structure 1 and the other anti-cancer active agents which provides for an enhanced effect in mitigating, interfering with and/or reversing the proliferation of melanoma and/or non-melanoma skin cancer which allows for use of a lesser amount of the conventional agent to achieve the same effect as attained by the conventional agent on its own. These compositions may further contain other ingredients commonly co-administered with anti-cancer therapeutic active agents in conventional amounts.

In accordance yet another aspect of the present teaching there are provided methods for the treatment of non-melanoma and/or melanoma skin cancers said method comprising administering, topically, orally, intravenously, intraperitoneally and/or subcutaneously, a therapeutically effective amount of a composition comprising at least one compound according to Structure 1 for interfering with, inhibiting or reversing the proliferation of non-melanoma and/or melanoma skin cancer. Typically, and preferably, these compositions also comprise and a suitable carrier, especially a pharmaceutically acceptable carrier, for the method of administration, Additionally, these compositions may have the one or more compounds of Structure 1 as the sole anti-cancer active agent or they may further comprise one or more other anti-cancer therapeutic, especially immuno- and/or chemo-therapeutic active agents, known or believed or suspected to be suitable for use in the treatment of non-melanoma and/or melanoma skin cancers and/or one or more other ingredients commonly co-administered with anti-cancer therapeutic active agents. Preferably, the amount of the compound(s) according to Structure 1 in such compositions is from 0.05 to 25 percent, preferably from 0.1 to 20 percent, more preferably from 0.5 to 15 percent by weight based on the total weight of the composition. The other anti-cancer agents are present in their conventional therapeutically effective amounts; however, as there appears to be a level of synergy that arises with the combination of compounds according to Structure 1 and the other anti-cancer active agents which provides for an enhanced effect in mitigating, interfering with and/or reversing the proliferation of melanoma and/or non-melanoma skin cancer, one may use of a lesser amount of the conventional agent to achieve the same desired effect as just the conventional agent on its own. The other ingredients commonly co-administered with anti-cancer therapeutic active agents are present in conventional amounts.

DETAILED DESCRIPTION

Figure 1:
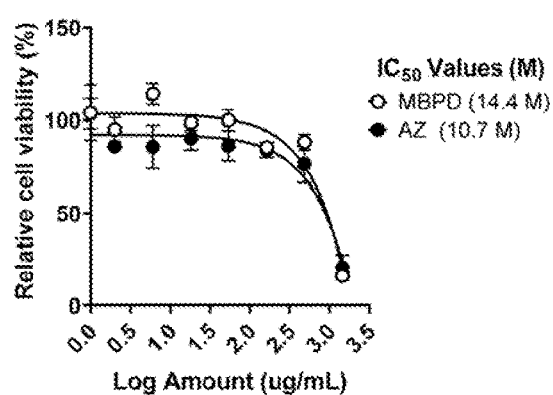
FIG. 1 is a graph plot of the cell viability of darkly pigmented normal mouse melanocytes to increasing concentrations of acetyl zingerone and MBPD.

As used in the present specification, the following terms shall have the meanings as presented:

"Patient" refers to a human individual.

"Pharmaceutically acceptable" means that the subject of this descriptor has been approved or is otherwise approvable by a regulatory agency of a government or governmental or is listed in the U.S. Pharmacopoeia or other generally recognized pharmacopoeia for use on or in humans.

"Pharmaceutically acceptable carrier" refers to a pharmaceutically acceptable diluent, a pharmaceutically acceptable adjuvant, a pharmaceutically acceptable excipient, a pharmaceutically acceptable vehicle or carrier, or a combination of any of the foregoing with which a pharmacological active agent, including the compounds provided by the present disclosure, can be administered to a patient, which does not destroy or have a marked adverse effect on the pharmacological activity of the therein contained pharmacological active agent or metabolite thereof and which is preferably non-toxic or of acceptable toxicity when administered in doses sufficient to provide a therapeutically effective amount of the pharmacological active agent or metabolite thereof.

"Pharmaceutical composition" refers to a composition comprising a pharmaceutically acceptable carrier and a pharmacological active agent or metabolite, especially, in the case of pharmaceutical compositions claimed by the present application.

"Treating" or "treatment" of any disease refers to reversing, alleviating, arresting, inhibiting, interfering and/or ameliorating the appearance and/or proliferation of a disease or at least one of the clinical symptoms of a disease, inhibiting the progress of a disease or at least one of the clinical symptoms of the disease as well as delaying the onset of a disease or at least one or more symptoms thereof in a patient who is predisposed to a disease, especially as evidenced by genetic testing, even though that patient does not yet experience or display symptoms of the disease. In following, treating or treatment also refers to inhibiting a disease, either physically, (e.g., stabilization of a discernible symptom), physiologically, (e.g., stabilization of a physical parameter), or both, and to inhibiting at least one physical parameter that may or may not be discernible to the patient.

"Improve" or "improvement" is used to convey the fact that the pharmacological active agent has manifested or effected changes, most notably beneficial changes, in either the characteristics and/or the physical attributes of the tissue to which it is being provided, applied or administered, including, e.g., necrosis of skin cancer cells. These terms are also used to indicate that the symptoms or physical characteristics associated with the diseased state are diminished, reduced, or eliminated.

"Inhibiting" generally refers to delaying the onset of the symptoms, delaying, or stopping the progression of the disease and/or its manifestation symptoms, alleviating the symptoms, or eliminating the disease, condition, or disorder.

"Optional" or "optionally" means that the subsequently described subject, event or circumstance is not required or a necessary consequence, and that the description includes instances where the event occurs and instances where it does not and/or when the subject is present and when it is not present.

"Therapeutically effective amount" refers to the amount of a compound or composition that, when administered to a patient for treating a disease, or at least one of the clinical symptoms of a disease, is sufficient to affect such treatment of the disease or symptom thereof. The "therapeutically effective amount" varies depending, for example, on the compound or composition, the disease and/or symptoms of the disease, the severity of the disease and/or symptoms of the disease, the age, weight, and/or health of the patient to be treated, the mode of administration, the presence of synergistic agents, the judgment of the prescribing physician and the like. An appropriate amount of any given compound or composition can be ascertained by those skilled in the art and/or is capable of determination by routine experimentation.

"Therapeutically effective dose" refers to a dose that provides a therapeutically effective amount of the given agent to provide effective treatment of a disease in a patient. A therapeutically effective dose varies from compound/composition to compound/-composition and/or from patient to patient and depends upon factors such as the condition of the patient and the route of delivery as well as those described in the preceding definition of therapeutically effective amount. A therapeutically effective dose can be determined in accordance with routine pharmacological procedures known to those skilled in the art. A therapeutic effective dose also contemplates the use of an initial or charging dose followed by sequent doses, daily, weekly or whatever, wherein the quantity of the active agent in the initial dose is greater than in the subsequent doses.

Erring on the side of caution and to avoid having overlooked or inadvertently omitted certain descriptive matter, particularly complementary and supplementary descriptive matter, Applicant hereby states and affirms that the technical publications as well as the patent and patent application publications mentioned herein are all incorporated herein in their entirety by this reference. Indeed, for example, while Applicant could present page after page of description of suitable pharmaceutically acceptable vehicles, such would not be productive as the same are well known and well recognized by those skilled in the art and those that come into being after the filing of this application will readily be appreciated as suitable as well. The same holds true for many other potential constituents, both active and non-active, that are employed in pharmaceutical compositions made in accordance with the present teachings.

According to the present teaching, it has now been found that certain aryl alkanones according to Structure 1

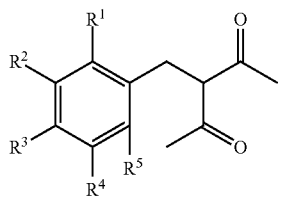

wherein $R_1$, $R_2$, $R_3$, $R_4$ and $R_5$, which may be the same or different, are each independently H, OH, alkyl or alkoxy; preferably H, OH or alkoxy; provided that at least one of $R_1$, $R_2$, $R_3$, $R_4$ and $R_5$ is not H, and wherein the alkyl or alkoxy groups, if present, are linear or branched and have from 1 to 8 carbon atoms, preferably from 1 to 6 carbon atoms, most preferably from 1 to 4 carbon atoms, are very effective in up-regulating genes that are adversely affected by, particularly down regulated by, non-melanoma skin cancers and/or melanoma and in down-regulating genes that are otherwise up-regulated by non-melanoma skin cancers and melanoma as well as in the treatment of such skin cancers. In particular, it has been found that these compounds are effective in mitigating, interfering with and/or reversing the proliferation, including metastasization, of non-melanoma and melanoma skin cancers, particularly in humans. Preferably, the compounds of Structure 1 are those wherein $R_1$ and $R_2$ are H and $R_3$, $R_4$ and $R_5$, which may be the same or different, are each independently H, OH, or $C_1$ to $C_4$ alkoxy, provided that at least one of $R_3$, $R_4$ and $R_5$ is not H.

In following, in accordance with one aspect of the present teaching there are provided topical, oral, intravenous, intraperitoneal and/or subcutaneous administrable compositions comprising at least one compound according to Structure 1. Typically, and preferably, these compositions further comprise a carrier suitable for the given mode of administration, preferably a pharmaceutically acceptable carrier. Preferably, the amount of the compound(s) according to Structure 1 in such compositions is from 0.05 to 25 percent, preferably from 0.1 to 20 percent, more preferably from 0.5 to 15 percent by weight based on the total weight of the composition. These compositions may further contain other ingredients commonly co-administered with anti-cancer therapeutic, especially immune-, and chemo-therapeutic, active agents in conventional amounts.

In accordance with a second aspect of the present teaching there are provided topical, oral, intravenous, intraperitoneal and/or subcutaneous administrable compositions comprising at least one compound according to Structure 1 in combination with at least one other anti-cancer therapeutic, especially immuno- and/or chemo-therapeutic, active agents. Typically, and preferably, these compositions further comprise a suitable carrier, preferably a pharmaceutically acceptable carrier. The other anti-cancer active agents are those known or believed or suspected to be suitable for use in the treatment of non-melanoma and/or melanoma skin cancers. Exemplary anti-cancer active agents include, but are not limited to, dacarbazine; AMPK activator; immune checkpoint inhibitors (ICI): BRAE and MEK inhibitors, including dabrafenib (Tafinlar), trametinib (Mekinist), vemurafenib (Zelboraf), cobimetinib (Cote encorafenib (Braftovi) and binimetinib (Mektovi); PD-1 inhibitors, including pembrolizumab (Keytruda) and nivolumab (Opdivo); CTLA-4 inhibitors, including ipilimumab (Yervoy), and the like, as well as combinations of any two or more of the foregoing. Indeed, suitable combinations of such anti-cancer active agents are already well known and/or in development. Preferably, the amount of the compound(s) according to Structure 1 in such compositions is from 0.05 to 25 percent, preferably from 0.1 to 20 percent, more preferably from 0.5 to 15 percent by weight based on the total weight of the composition. The other anti-cancer agents are present in their conventional therapeutically effective amounts; however, as there appears to be a level of synergy that arises with the combination of compounds according to Structure 1 and the other anti-cancer active agents which provides for an enhanced effect in mitigating, interfering with and/or reversing the proliferation of melanoma and/or non-melanoma skin cancer such that one is able to use a lesser amount of the conventional agent to achieve the same effect as attained by the conventional anti-cancer active agent on its own. These compositions may further contain other ingredients commonly co-administered with anti-cancer therapeutic active agents in conventional amounts.

In accordance a third aspect of the present teaching there are provided methods for the treatment of non-melanoma and/or melanoma skin cancers said method comprising administering, topically, orally, intravenously, intraperitoneally and/or subcutaneously, to an individual human a therapeutically effective amount of a composition comprising at least one compound according to Structure 1 for treating melanoma and/or non-melanoma skin cancer, especially for interfering with, inhibiting or reversing the proliferation of non-melanoma and/or melanoma skin cancer. Typically, and preferably, the composition also a suitable carrier, preferably a therapeutically acceptable carrier, for the method of administration.

In accordance a fourth aspect of the present teaching there are provided methods for the treatment of non-melanoma and/or melanoma skin cancers said method comprising administering, topically, orally, intravenously, intraperitoneally and/or subcutaneously, a therapeutically effective amount of a composition comprising at least one compound according to Structure 1 and one or more other anti-cancer therapeutic, especially immuno- and/or chemo-therapeutic active agents, known or believed or suspected to be suitable for use in the treatment of non-melanoma and/or melanoma skin cancers for treating, especially interfering with, inhibiting or reversing the proliferation of, non-melanoma and/or melanoma skin cancer. Typically, and preferably, the composition also a suitable carrier, preferably a therapeutically acceptable carrier, for the method of administration.

In accordance a fifth aspect of the present teaching there are provided methods for the treatment of non-melanoma and/or melanoma skin cancers said method comprising administering, topically, orally, intravenously, intraperitoneally and/or subcutaneously, a therapeutically effective amount of a composition comprising at least one compound according to Structure 1 for treating, especially for interfering with, inhibiting or reversing the proliferation of, non-melanoma and/or melanoma skin cancer while also administering a therapeutically effective amount of one or more other anti-cancer therapeutic, especially immuno- and/or chemo-therapeutic active agents, known or believed or suspected to be suitable for use in the treatment of non-melanoma and/or melanoma skin cancers, wherein both agents are administered separately, but concurrently, or wherein one is administered prior to or subsequent to the other, but essentially in the same treatment regime. In this regard, such administration of the two anti-melanoma and/or anti-non-melanoma skin cancer active agents may be staggered, alternated, in a series of one then a series of the other, etc.: the gist of this aspect of the claimed invention being that the treatment regime includes the separate administration of both the one or more compounds of Structure 1 and the one or more other anti-cancer therapeutic, especially immuno- and/or chemo-therapeutic active agents. In this method it is often desirable to separately administer other pharmaceutically active agents commonly co-administered with anti-cancer therapeutic active agents, including, especially antiemetic agents such as anti-nausea agents, antacid agents, and the like, in conventional amounts.

In each of the foregoing methods, the amount of the compound(s) according to Structure 1 in such compositions is typically from 0.05 to 25 percent, preferably from 0.1 to 20 percent, more preferably from 0.5 to 15 percent by weight based on the total weight of the composition. Similarly, the amount of the other anti-cancer agents in said compositions is generally that amount which is conventional for their use. However, lesser amounts of the latter may be used due to a level of synergy that arises with the combination of compounds according to Structure 1 and the other anti-cancer active agents. Specifically, the combination provides for an enhanced effect in mitigating, interfering with and/or reversing the proliferation of melanoma and/or non-melanoma skin cancer as compared to the other anti-cancer active agent or combination of such agents in the absence of the compound(s) of Structure 1. Alternatively, one may use a lesser amount of the other anti-cancer active agent to achieve the same desired effect. In terms of a total regimen of administrations, the synergy may also shorten the duration of and/or reduce the number of doses of the compositions during the treatment regime. Finally, the compositions provided in the aforementioned methods may further contain or be concurrently administered with other ingredients commonly co-administered with anti-cancer therapeutic active agents in conventional amounts.

As noted, the most critical component of the compositions and methods of the present teaching is the compound(s) according to Structure 1

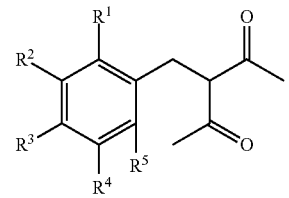

wherein $R_1$, $R_2$, $R_3$, $R_4$ and $R_5$, which may be the same or different, are each independently H. OH, alkyl or alkoxy; preferably H, OH or alkoxy; provided that at least one of $R_1$, $R_2$, $R_3$, $R_4$ and $R_5$ is not H, and wherein the alkyl or alkoxy groups, if present, are linear or branched and have from 1 to 8 carbon atoms, preferably from 1 to 6 carbon atoms, most preferably from 1 to 4 carbon atoms. Preferably the compounds of Structure 1 are those wherein Re $R_2$, $R_3$, $R_4$ and $R_5$ are H, OH or alkoxy, more preferably, those wherein $R_1$ and $R_2$ are H and $R_3$, $R_4$ and $R_5$, which may be the same or different, are each independently H, OH, or $C_1$ to $C_4$ alkoxy, provided that at least one of $R_2$, $R_3$, $R_4$ and $R_5$ is not H. Especially preferred compounds are those wherein $R_1$ is H and $R_2$, $R_3$, $R_4$ and $R_5$, which may be the same or different, are each independently H, OH, or $OCH_3$; provided at least one or two of $R_2$, $R_3$, $R_4$ and $R_5$ is OH or $OCH_3$ or one of $R_2$, $R_3$, $R_4$ and $R_5$ is OH and at least one of the remaining moieties is OH or $OCH_3$, preferably $OCH_3$. More preferably $R_1$ and $R_2$ are H and $R_3$, $R_4$ and $R_5$, which may be the same or different, are each independently H, OH, or $OCH_3$; provided at least one or two of $R_3$, $R_4$ and $R_5$ is OH or $OCH_3$ or one of $R_3$, $R_4$ and $R_5$ is OH and at least one of the remaining moieties is OH or $OCH_3$, preferably $OCH_3$. Exemplary preferred compounds according to Structure 1 are as follows:

Compound 1: $R_1=R_2=R_5=H$; $R_3=OH$; and $R_4=OCH_3$;
Compound 2: $R_1=R_2=R_4=R_5=H$; and $R_3=OCH_3$;
Compound 3: $R_1=R_2=R_4=R_5=H$; and $R_3=OH$;
Compound 4: $R_1=R_2=R_3=R_5=H$; and $R_4=OH$;
Compound 5: $R_1=R_2=R_3=R_5=H$; and $R_4=OCH_3$;
Compound 6: $R_1=R_2=R_3=R_4=H$; and $R_{5=0}H$;
Compound 7: $R_1=R_2=R_3=R_4=H$; and $R_5=OCH_3$; and
Compound 8: $R_1=R_3=R_5=H$; and $R_2=R_4=OH$;

As noted above, the compositions of the present teaching and the methods of their use may further include one or more one other anti-cancer therapeutic, especially immuno- and/or chemo-therapeutic, active agents, in a suitable carrier. The other anti-cancer active agents are those known or believed or suspected to be suitable for use in the treatment of non-melanoma and/or melanoma skin cancers. Exemplary anti-cancer active agents include, but are not limited to, dacarbazine; AMPK activators, including AICAR (5-aminoimidazole-4-carboxamide-ribonusleoside; immune checkpoint inhibitors (ICI); BRA F and MEK inhibitors, including dabrafenib (Tafinlar), trametinib (Mekinist), vemurafenib (Zelboraf), cobimetinib (Cotellic), encorafenib (Braftovi) and binimetinib (Mektovi); PD-1 inhibitors, including pembrolizumab (Keytruda) and nivolumab (Opdivo); CTLA-4 inhibitors, including ipilimumab (Yervoy), and the like, as well as combinations of any two or more of the foregoing. Exemplary combinations of such anti-cancer active agents include, but are not limited to, combination regimens of BRAF and MEK inhibitors, a combination of nivolumab (Opdivo) and ipilimumab (Yervoy), dabrafenib (Tafinlar) plus trametinib (Mekinist), vemurafenib (Zelboraf) plus cobimetinib (Cotellic), and encorafenib (Braftovi) plus binimetinib (Mektovi) as well as other combinations of MEK inhibitions with CDK4/6 inhibitors, pan-RAF inhibitors, and/or PI3K inhibitors, among others.

These other anti-cancer active agents may be combined with the compounds of Structure 1 to form a single composition for administration, or they may be used in combination with compositions containing the compounds of Structure 1 but administered separately. They are administered in conventional therapeutically effective amounts for the specific agent and method or mode of administration or, as noted above, may be used at lesser amounts due to synergy between these other anti-cancer agents and the compounds of Structure 1, as discussed elsewhere herein.

Similarly the compositions of the present teaching, whether having the compounds of Structure 1 as the sole active agent or in combination with other anti-cancer active agents, may further comprise one or more other non-anti-cancer actives used to address the ill effects/side effects of the anti-cancer treatments and the like. Depending upon the nature and/or purpose of these other non-anti-cancer agents, they may be combined in a single composition with the compounds of Structure 1 and/or the other anti-cancer active agents. More commonly and preferably, they are administered separately prior to, concurrent with and/or subsequent to the administration of the anti-cancer agents. Such other non-anti-cancer agents include antiemetics, especially anti-nausea agents, anti-seizure agents, antacids, and the like. These non-anti-cancer actives are administered in conventional therapeutically effective amounts for the specific agent and method or mode of administration.

As discussed, the foregoing compositions are effective in the treatment of melanoma and non-melanoma skin cancers. These compositions are typically formulated in a unit dosage form, i.e., physically discrete units suitable as a unitary dose for patients undergoing treatment, with each unit containing a predetermined quantity of the active agents, specifically the compound(s) of Structure 1, alone or in combination with other anti-cancer active agents, as discussed above, calculated to produce an intended therapeutic effect. A unit dosage form can be for a single daily dose, for administration 2 times per day, or one of multiple daily doses, e.g., 3 or more times per day. When multiple daily doses are used, a unit dosage form can be the same or different for each dose. One or more dosage forms typically comprise a dose, which can be administered to a patient at a single point in time or during a time interval.

Following on the foregoing, the amount of a compound of Structure 1 contained in a dose depends upon, among other factors, the route of administration and whether the state or stage of the disease. In any event, the administered dose is typically less than a toxic dose: though it may have significant adverse health effects, provided that the desired beneficial effect is also attained. Toxicity of the compositions described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a compound or metabolite thereof may exhibit a high therapeutic index. The data obtained from these cell culture assays, and animal studies can be used in formulating a dosage range that is not toxic for use in humans. A dose of a compound of Formula (I) is typically set within a range of circulating concentrations in the blood serum or lymphatic fluid, that include the effective dose and that exhibits little or no toxicity. A dose can vary within this range depending upon the dosage form employed and the route of administration utilized. In certain embodiments, an escalating dose can be administered.

The pharmaceutical compositions of the present teaching can be formulated for immediate release or for delayed or controlled release. In this latter regard, certain embodiments, e.g., an orally administered product, can be adapted for controlled release. Controlled delivery technologies can improve the absorption of a drug in a particular region, or regions, of the gastrointestinal tract. Controlled drug delivery systems are designed to deliver a drug in such a way that the drug level is maintained within a therapeutically effective window and effective and safe blood levels are maintained for a period if the system continues to deliver the drug with a particular release profile in the gastrointestinal tract. Controlled drug delivery typically and preferably produces substantially constant blood levels of a drug over a period as compared to fluctuations observed with immediate release dosage forms. For some drugs, maintaining a constant blood and tissue concentration of the drug throughout the course of therapy is the most desirable mode of treatment as immediate release of drugs oftentimes causes blood levels to peak above that level required to elicit a desired response. This results in waste of the drug and/or may cause or exacerbate toxic side effects. In contrast, the controlled delivery of a drug can result in optimum therapy; not only reducing the frequency of dosing, but also reducing the severity of side effects. Examples of controlled release dosage forms include dissolution-controlled systems, diffusion controlled systems, ion exchange resins, osmotically controlled systems, erodable matrix systems, pH independent formulations, and gastric retention systems.

Though the mode of administration has been characterized above as being topical, oral, intravenous, intraperitoneal, and/or subcutaneous administrable (which essentially covers all routes of administration), it is to be appreciated that this characterization is not intended to be limiting. Indeed, the compositions of the present teaching can be administered through any conventional method. The specific mode of application or administration is, in part, dependent upon the form of the pharmaceutical composition, the primary purpose or target of its application (e.g., the application may be oral if intending to address the disease generally or topically if intending to address primarily a topical symptom or location of the disease, Specific suitable modes of administration include, for example, intradermal, intramuscular, intraperitoneal, intravenous, subcutaneous, intranasal, epidural, oral, sublingual, intracerebral, intravaginal, transdermal, rectal, or inhalation. Especially preferred modes of administration are oral, topical, intravenous, or intraperitoneal. Indeed, depending upon the stage of the melanoma or non-melanoma skin cancer the best mode of administration may be local to the site of the cancer or systemic, especially if the cancer has spread. Finally, the form of the pharmaceutical composition and its delivery system varies depending upon the parameters already noted. For example, orally administered pharmaceutical compositions of the present teaching can be in encapsulated form, e.g., encapsulated in liposomes, or as microparticles, microcapsules, capsules, etc. Of course, such encapsulation may be necessary if the compounds of Structure 1 or, if present the other anti-cancer actives are subject to adverse action, degradation, metabolism by the fluids and physiological processes of the stomach and/or intestines. Indeed, such problems may dictate the use of alternate modes of administration.

As also noted above, the concentration of the compounds of Structure 1 in the pharmaceutical composition is from 0.05 to 25 percent, preferably from 0.1 to 20 percent, more preferably from 0.5 to 15 percent by weight based on the total weight of the composition; however, even these ranges may vary, and certainly the specific concentration varies within these ranges as the dose or rate of application of the compounds to the patient will also affect the concentration. Obviously, dosing itself depends upon several factors including the concentration and/or purity of the compounds of Structure 1 the efficacy thereof, the individual to whom the pharmaceutical is to be administered, the mode of administration, the form in which the pharmaceutical composition is to be administered, the severity or extent and/or spread of the disease, etc.

The foregoing factors as well as the application thereof in formulating the compositions of the present teaching are all as well known in the art whereby the final or actual concentration in the pharmaceutical composition and/or the dose can readily be determined based up simple dose-response testing and the like. For example, an appropriate oral dosage for a particular pharmaceutical composition containing one or more compounds of Structure 1 will depend, at least in part, on the gastrointestinal absorption properties of the compound, the stability of the compound in the gastrointestinal tract, the pharmacokinetics of the compound and the intended therapeutic profile.

Following on the foregoing, an appropriate controlled release oral dosage and ultimate form of a pharmaceutical composition containing a particular compound of Structure 1 will also depend upon a number of factors. For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Again, it is to be expected that certain compounds are absorbed primarily from the small intestine whereas others are absorbed primarily through the large intestine. It is also to be appreciated that while it is generally accepted that compounds traverse the length of the small intestine in about 3 to 5 hours, there are compounds that are not easily absorbed by the small intestine or that do not dissolve readily. Thus, in these instances, the window for active agent absorption in the small intestine may be too short to provide a desired therapeutic effect in which case large intestinal absorption must be channeled and/or alternate routes of administration pursued.

Generally speaking, an appropriate dose of a compound of Structure 1, or pharmaceutical composition comprising a compound of Structure 1, can be determined according to any one of several well-established protocols including in-vitro and/or in-vivo assays and/or model studies as well as clinical trials. For example, animal studies involving mice, rats, dogs, and/or monkeys can be used to determine an appropriate dose of a pharmaceutical compound. Results from animal studies are typically extrapolated to determine appropriate doses for use in other species, such as for example; humans.

EXPERIMENTAL

Example 1—Cell Viability in Normal Melanocytes v. Melanoma Cells

In support of the present teachings several experiments were conducted to assess the cytotoxicity of compound 1 (Acetyl Zingerone CAT), available as Synoxyl® AZ from Sytheon Ltd.) and Compound 4, its mono-methoxy analog (3-(4-Methoxy-benzyl)-pentane-2,4-dione (MBPD)), towards normal melanocytes (Normal, C57BL/6 mouse melanocytes, darkly pigmented), and patient derived, NRAS-mutated melanoma cells. On Day 1, the melanoma cells and normal melanocytes were seeded into the black walled 96 well plates (cat. no.—165305, thermo), ~1000 cells per well and allowed to stand for one day. The normal melanocytes were cultured in OptiMem base medium (Cat. 31985-070, Life Technologies, Carlsbad, CA) supplemented with 7% horse serum (Cat. 100-508, Gemini Bio-Products, W. Sacramento, CA), and 10 ng/ml (16.2 nM) TPA (12-O-tetradecanoylphorbol-13-acetate, Cat. P1585, Sigma, St. Louis, MO) and the melanoma cells were cultured in OptiMem supplemented with 5% horse serum (Cat. 100-500, Gemini Bio-Products, W. Sacramento, CA), no TPA. On Day 2, the cell plates were treated with various amounts/concentrations of AZ and MBPD (0, 2, 6, 18, 54, 162, 486, 1458 µg/ml), which was added directly into the cell culture medium. On Day 5, Alamar blue (cat. no. A50101, Invitrogen) was added in each well and incubated for 1 hr in $CO_2$ incubator to differentiate between the live and dead cells: Alamar blue stains only the live cells. Thereafter, the dye was replaced with 100 ul PBS (Cat. no. 14190-144, Gibco) and cell viability as evidenced by fluorescence was recorded (by Biotek synergy/H1 microplate reader) at 560/590 nm. Cell survival was calculated by subtracting the background (media only) and then normalizing those results with the results obtained from the cells that were not treated with AZ or MBPD.

Figure 2:
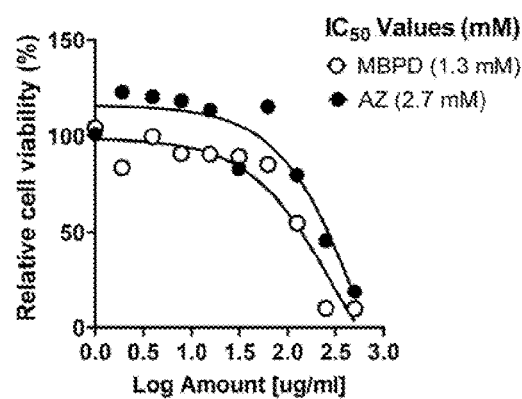
FIG. 2 is a graph plot of the cell viability of patient derived, NRAS-mutated melanoma cells to increasing concentrations of acetyl zingerone and MBPD.

The results of this first series of experiments are presented in graphic form in FIGS. 1 (4 biological repeats) and 2 (3 biological repeats) for the normal melanocytes and melanoma cells, respectively. In these figures, the X-axis shows the amounts used in µg/ml, Molar (M) $IC_{50}$ values were calculated using formula weight of each of the compounds individually. The results shown in FIG. 1 demonstrate that neither AZ nor MBPD were cytotoxic until extremely high levels were present. Based this data, $IC_{50}$ values of these analogs were calculated to be AZ=10.7 M and MBPD=14.4 M in normal, pigmented melanocytes. In sharp contrast, as shown in FIG. 2, both AZ and MBPD demonstrated a marked toxicity to the melanoma cells. As indicated, here these same analogs killed the NRAS-mutated, patient derived melanoma cells at significantly low concentrations with $IC_{50}$ values at 1.3 mM for AZ and 0.4 mM for MBPD. These results demonstrate the marked ability and specificity of the compounds according to Structure 1 as efficacious anti-cancer treatments for use in the treatment of melanoma and non-melanoma skin cancers, without concern as to cytotoxicity of other cells, particularly keratinocytes.

Example 2—MBPD/Trametinib Synergy

Another series of experiments were conducted similar to those of Example 1 in an effort to assess synergies between the compounds of Structure 1 and known melanoma treatments. Here, the compounds of Structure 1 were further challenged by isolating melanoma cells that were essentially resistant to the known agent and assessing the supplementary or synergistic behavior of the compounds of Structure 1. Specifically, Trametinib resistant human, NRAS mutated, WM1366 melanoma cells were created in-house by sequentially treating the cells with various concentrations (2 nM-10 nM) of Trametinib for several weeks. Those cells which survived 2 nM Trametinib after two weeks, were then incubated with 4 nM Trametinib and those that survived 4 nM Trametinib for two weeks were isolated and then incubated with 10 nM for several weeks. This led to development of resistance in the WM1366 cells. We used these "in-house generated, Trametinib resistant, NRAS-mutated melanoma cells (Trametinib $IC_{50}$=~10-20 nM).

In this study, the Trametinib resistant cells were seeded into black walled 96 well plates (cat. no.—165305, thermo), ~1000 cells per well employing the same media as noted in Example 1. On Day 2, the cells were treated with 125 or 62.5 μg/ml MBPD and incubated for 48 hours. After 48 hours, fresh cell-culture medium was added with MBPD and Trametinib at concentrations of 30, 15, 7.5, 3.75, 1.875, and 0.9375 nM and the cells allowed to sit for 72 hours. On Day 7, Alamar blue (cat. no. A50101, invitrogen) was added to each well and the cultures incubated for 1 hr in a $CO_2$ incubator. Thereafter, the dye was replaced with 100 ul PBS (Cat no. 14190-144, Gibco) and cell viability as evidenced by fluorescence was recorded (by Biotek synergy/H1 microplate reader) at 560/590 nm. Cell survival was calculated by subtracting the background (media only) and then normalizing those results with the results obtained from the cells that were not treated with MBPD.

Figure 3:
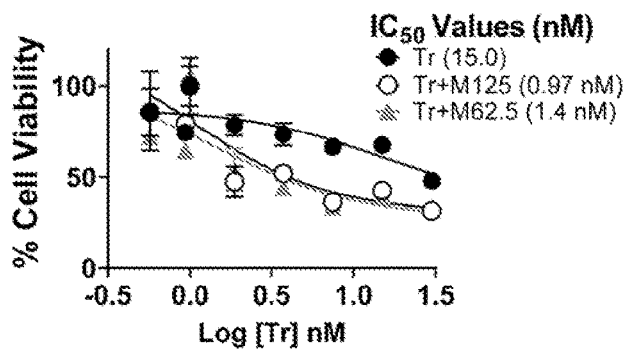
FIG. 3 is a graph plot of the cell viability of in-house developed, Trametinib resistant, NRAS-mutated melanoma cells to increasing concentrations of trametinib and combinations thereof with MBPD.

The results of this series of experiments are presented in graphic form in FIG. 3: the data points representing 2 biological repeats. As in the prior figures, the X-axis shows the amounts used in μg/ml. Molar (M) $IC_{50}$ values were calculated using formula weight of each of the compounds individually. The results shown in FIG. 3 demonstrate the marked synergy of MBPD, at both low and higher levels, with Trametinib in killing melanoma cells. As calculated, MBPD reduced the Trametinib $IC_{50}$ by ~5 fold: clearly a marked, synergistic improvement in efficacy: this in cells that were already pre-conditioned to be resistant or resistive to Trametinib.

Example 3—AMPK Activation

AMPK activation is a known and efficacious treatment for melanoma and non-melanoma skin cancer (See. e.g., Chen. L. et. al., "AMPK Activation by GSK621 Inhibits Human Melanoma Cells In Vitro and In Vivo", Biochemical and Biophysical Research Communications 480 (2016), 515-521). To ascertain the ability and efficacy of the compounds of Structure 1 to activate AMPK, a cell assay study was undertaken. In the study, human epidermal keratinocytes were grown using EpiLife Media (60 μM calcium) supplemented with 0.2% v/v bovine pituitary extract, 1 μg/ml recombinant human insulin-like growth factor-I, 0.18 μg/ml hydrocortisone, 5 μg/ml bovine transferrin, 0.2 ng/ml human epidermal growth factor. The cells were grown at 37±2° C. and 5±1% $CO_2$. The keratinocytes were seeded into 96-well plates and cultured overnight to allow the cells to adhere to the well plates. Prior to experimental use, the growth media was replaced with basal media (unsupplemented EpiLife Media) for five hours prior to starting any treatments. The test materials and the positive control (resveratrol) were prepared as stock solutions in DMSO: all treatments in the study, including the non-$H_2O_2$ exposed and untreated group, had a final concentration of 0.5% DMSO.

The ability of the test material to activate AMPK was determined by measuring the phosphorylation of AMPK. The epidermal keratinocytes were treated with the test material prepared in basal media for two hours. At the end of the two-hour incubation the culture media was removed and the cells were fixed in 4% formaldehyde for 20 minutes at room temperature. After the fixation, the cells were washed three times with wash solution (1 minute per wash) and any endogenous peroxidase activity was quenched by adding 100 ul of a 0.3% $H_2O_2$ solution to the wells and incubating the plate for another 20 minutes. After washing as described above, non-specific antibody binding was blocked by adding 200 ul of blocking buffer to each well and incubating the plate for 1 hour at room temperature. After blocking, 100 ul of an antibody solution which recognizes AMPK phosphorylated at Thr-172 was added to each well and the plate was incubated overnight at 4° C. and then washed as described above. After this wash, 100 ul of a secondary antibody solution was added to the wells and the plate was incubated for 90 minutes at room temperature. After washing again as described above, 50 ul of a fluorescent substrate solution was added to each well and the plate was incubated for 30 minutes at room temperature in the dark. After this incubation, 50 ul of a protein reactive fluorescent stain was added to the well plate and the plate was incubated for an additional 5 minutes at room temperature in the dark. After this incubation the well plate was read using a fluorometer at 530ex/590em to determine AMPK phosphorylation and at 360ex/485em to determine total cellular protein.

The results are presented in Table 1. As noted, even low levels of AZ were found to activate AMPK; however, a modestly higher level, 50 μg/ml provided a marked effect on AMPK activation, increasing AMPK activity by 88.3%, Based on the known anti-melanoma effect of AMPK activation, it is clear that AZ presents itself as an efficacious anti-melanoma treatment.

TABLE 1

| AMPK Activation Study | |
|---|---|
| Treatment | AMPK-P/Protein Ratio |
| Cells non-$H_2O_2$ treated | 3.44 ± 0.38 |
| Cells treated with $H_2O_2$ | 3.35 ± 0.50 |
| Synoxyl AZ 50 μg/ml | 6.48 ± 1.10 |
| Synoxyl AZ 25 μg/ml | 4.16 ± 0.65 |

The foregoing effect of AZ as an AMPK activator and, in turn, anti-melanoma treatment is especially surprising in light of the pro-viability effect of AZ in normal cells, even those in senescence. Specifically, following on the foregoing experimental methodology, additional studies were conducted on the human keratinocytes cells to assess AZ's impact on cell viability as evidenced by an MTT assay as well as an assessment of its impact on SA-B-Gal activity. In these studies, the human epidermal keratinocytes were treated in basal media for two hours with the test material and then treated with either 50 uM or 100 uM $H_2O_2$ in basal media for an additional two hours: the latter treatment to induce senescence. Following the $H_2O_2$ treatment, the cells were placed in with fully supplemented EpiLife media for either 16 hours after which changes in cell viability was evaluated via an MTT assay or for 3 days after which changes in the cellular senescence marker beta galactosidase (SA-B-GAL) was evaluated.

MTT Calculation: the mean MIT absorbance value for untreated cells not exposed to $H_2O_2$ was calculated and used to represent 100% cell viability. The individual MIT values from the cells undergoing the various treatments was then divided by the mean value for the untreated cells not exposed to H2O2 and expressed as a percent to determine the change in cell viability caused by each treatment.

SA-B-GAL Calculation: To determine the changes in SA-B-GAL expression a direct measure of SA-B-GAL activity was used. At the end of the three-day incubation the media was removed, 100 ul of ice-cold cell lysis buffer was added and the cells were lysed for 5 minutes at 4° C. At the end of this lysis procedure a portion of the lysate was used for a protein assay while 50 ul of the cell lysate was transferred to a new well plate and combined with an equal volume of SA-B-GAL reaction buffer containing a fluorescent substrate. This well plate was then incubated for 3 hours at 37° C., after which a 50 ul sample of the reaction was combined with 200 ul of stop solution in a new well plate and the plate was read using a fluorometer (360ex/485em), The fluorescence intensity was then normalized to cellular protein and this ratio was used as an index of SA-B-GAL activity.

The results of the MIT assay and SA-B-GAL activity studies re presented in Tables 2 and 3, respectively.

TABLE 2

MTT Assay (Cell Viability)

| | Viability (% of non-H2O2 exposed cells) | |
|---|---|---|
| Treatment | 100 μM $H_2O_2$ | 50 μM $H_2O_2$ |
| Cells non-$H_2O_2$ treated | 100 ± 6.2 | 100.0 ± 3.2 |
| Cells treated with $H_2O_2$ | 74.9 ± 3.6 | 82.4 ± 7.7 |
| Synoxyl AZ 50 μg/ml | 100.2 ± 6.5 | 100.7 ± 8.3* |
| Synoxyl AZ 25 μg/ml | 77.4 ± 9.6 | 76.1 ± 6.9 |
| Synoxyl AZ 12.5 μg/ml | 79.1 ± 1.4 | 79.9 ± 11.5 |

TABLE 3

Senescent Associated β-Galactosidase (SA-B-Gal) Activity Assay

| | SA-B-Gal Activity/Protein | |
|---|---|---|
| Treatment | 100 μM $H_2O_2$ | 50 μM $H_2O_2$ |
| Cells non-$H_2O_2$ treated | 0.65 ± 0.05 | 0.60 ± 0.11 |
| Cells treated with $H_2O_2$ | 3.67 ± 0.36* | 3.4 ± 0.52* |
| Synoxyl AZ 50 μg/ml | 0.90 ± 0.15* | 0.91 ± 0.06* |
| Synoxyl AZ 25 μg/ml | 3.95 ± 0.36 | 3.30 ± 0.23 |
| Synoxyl AZ 12.5 μg/ml | 3.29 ± 0.37 | 3.45 ± 0.29 |

The results shown in Tables 2 and 3 demonstrate the pro-cell viability characteristic of AZ in normal cells: a result opposite to that seen with melanoma cells. Equally important is that these showings further support the non-toxicity of AZ to normal cells whereby its use in melanoma and non-melanoma skin cancer treatment will not adversely affect other cells as also supported by Example 1 above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

We claim:

1. A method for the treatment of non-melanoma and/or melanoma skin cancers said method comprising administering, topically, orally, intravenously, intraperitoneally and/or subcutaneously, a therapeutically effective amount of (a) a composition comprising at least one compound according to Structure 1

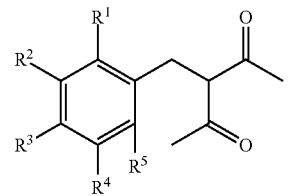

wherein $R_1$, $R_2$, $R_3$, $R_4$ and $R_5$, which may be the same or different, are each independently H, OH, alkyl or alkoxy, provided that at least one of $R_1$, $R_2$, $R_3$, $R_4$ and $R_5$ is not H, and wherein the alkyl or alkoxy groups, if present, are linear or branched and have, from 1 to 8 carbon atoms, alone or in combination with (b) at least one anti-cancer therapeutic active agent.

2. The method of claim 1 wherein $R_1$ and $R_2$ are H and $R_3$, $R_4$ and $R_5$, which may be the same or different, are each independently H, OH, or $C_1$ to $C_4$ alkoxy, provided that at least one of $R_3$, $R_4$ and $R_5$ is not H.

3. The method of claim 1 wherein $R_1$ and $R_2$ are H and $R_3$, $R_4$ and $R_5$, which may be the same or different, are each independently H, OH, or $OCH_3$; provided at least one or two of $R_3$, $R_4$ and $R_5$ is OH or $OCH_3$ or one of $R_3$, $R_4$ and $R_5$ is OH and at least one of the remaining moieties is OH or $OCH_3$.

4. The method of claim 1 wherein the at least one compounds according to Structure 1 is selected from the group consisting of:

Compound 1: $R_1=R_2=R_5=H$; $R_3=OH$; and $R_4=OCH_3$;
Compound 2: $R_1=R_2=R_4=R_5=H$; and $R_3=OCH_3$;
Compound 3: $R_1=R_2=R_4=R_5=H$; and $R_3=OH$;
Compound 4: $R_1=R_2=R_3=R_5=H$; and $R_4=OH$;
Compound 5: $R_1=R_2=R_3=R_5=H$; and $R_4=OCH_3$;
Compound 6: $R_1=R_2=R_3=R_4=H$; and $R_5=OH$;
Compound 7: $R_1=R_2=R_3=R_4=H$; and $R_5=OCH_3$; and
Compound 8: $R_1=R_3=R_5=H$; and $R_2=R_4=OH$.

5. The method of claim 1 wherein the at least one anti-cancer therapeutic active agent is also administered and is a compound or composition know or believed to be effective in treating melanoma and/or non-melanoma skin cancer.

6. The method of claim 5 wherein the at least one anti-cancer therapeutic active agent is selected from the group consisting of dacarbazine, an AMPK activator; an immune checkpoint inhibitor (ICI); a BRAF and/or MEK inhibitors, dabrafenib (Tafinlar), trametinib (Mekinist), vemurafenib (Zelboraf), cobimetinib (Cotellic), encorafenib (Braftovi), binimetinib (Mektovi), a PD-1 inhibitor, pembrolizumab (Keytruda), nivolumab (Opdivo), a CTLA-4 inhibitor, ipilimumab (Yervoy), and combinations of any two or more of the foregoing.

7. The method of claim 1 wherein the composition(s) further comprises a pharmaceutically acceptable carrier for the given mode of administration.

8. The method of claim 5 wherein the at least one compound according to Structure 1 and the at least one anti-cancer therapeutic active agent are administered at the same time, either as a single administration or in separate but concurrent administrations.

9. The method of claim 5 wherein the at least one compound according to Structure 1 and the at least one anti-cancer therapeutic active agent are administered separately at different times.

10. The method of claim 9 wherein the at least one compound according to Structure 1 and the at least one anti-cancer therapeutic active agent are administered separately at different times in a staggered or alternating regimen.

11. The method of claim 1 wherein the compound(s) according to Structure 1 is(are) present in an amount of from 0.05 to 25 percent by weight based on the total weight of the composition administered and containing the same.

12. The method of claim 1 wherein the compound(s) according to Structure 1 is(are) present in an amount of from 0.1 to 20 percent by weight based on the total weight of the composition administered and containing the same.

13. The method of claim 1 wherein the compound(s) according to Structure 1 is(are) present in an amount of from 0.5 to 15 percent by weight based on the total weight of the composition administered and containing the same.

14. The method of claim 1 wherein the other anti-cancer (agents) is present in its(their) conventional therapeutically effective amount(s).

15. The method of claim 11 wherein the other anti-cancer agent(s) is present in its(their) conventional therapeutically effective amount(s).

16. The method of claim 12 wherein the other anti-cancer agent(s) is present in its(their) conventional therapeutically effective amount(s).

17. The method of claim 13 wherein the other anti-cancer agent(s) is present in its(their) conventional therapeutically effective amount(s).

18. The method of claim 6 wherein the other anti-cancer therapeutic active agent is selected from the group consisting of dabrafenib (Tafinlar), trametinib (Mekinist), vemurafenib (Zelboraf), cobimetinib (Cotellic), encorafenib (Braftovi), binimetinib (Mektovi), pembrolizumab (Keytruda), nivolumab (Opdivo), and ipilimumab (Yervoy).

19. The method of claim 6 wherein the other anti-cancer therapeutic active agent is trametinib (Mekinist).

20. The method of claim 6 wherein the other anti-cancer therapeutic active agent is pembrolizumab (Keytruda).

21. The method of claim (6) wherein the other anti-cancer therapeutic active agent is selected from a combination of nivolumab (Opdivo) and ipilimumab (Yervoy), a combination of dabrafenib (Tafinlar) and trametinib (Mekinist), a combination of vemurafenib (Zelboraf) and cobimetinib (Cotellic), and a combination of encorafenib (Braftovi) and binimetinib (Mektovi).

* * * * *